United States Patent [19]

Murray, Jr. et al.

[11] Patent Number: 5,107,118

[45] Date of Patent: Apr. 21, 1992

[54] MEASUREMENT OF WATER LEVELS IN LIQUID HYDROCARBON MEDIA

[75] Inventors: Richard C. Murray, Jr., Palatine; Christopher A. Mendyk, Carol Stream; Alan D. Wilks, Mt. Prospect, all of Ill.

[73] Assignee: UOP, Des Plaines, Ill.

[21] Appl. No.: 590,728

[22] Filed: Oct. 1, 1990

[51] Int. Cl.⁵ .............................. G01N 21/35
[52] U.S. Cl. .......................... 250/339; 250/343; 250/345; 250/301
[58] Field of Search ............ 250/343, 345, 339, 301

[56] References Cited

U.S. PATENT DOCUMENTS 4,306,152 12/1981 Ross et al. ..................... 250/343

OTHER PUBLICATIONS

N. M. Alekseeva & E. E. Yudovich, Zhurnal Prikladnoi Spektroskopii, 15, No. 6, 1076-9 (1971), "The Use of IR Spectroscopy for the Determination of the Amount of Dissolved Water in Liquid Hydrocarbons".

Primary Examiner—Carolyn E. Fields
Assistant Examiner—James E. Beyer
Attorney, Agent, or Firm—Thomas K. McBride; Eugene I. Snyder

[57] ABSTRACT

It has been determined that the symmetric stretching frequency of water at concentrations of 10 ppm and more in liquid hydrocarbons is effectively independent of the nature of the hydrocarbon. On this basis one can rapidly, accurately, and precisely measure such water concentrations by comparing the transmittance of a narrow band of infrared frequencies within the symmetric stretching band of a wet sample with the transmittance at a frequency in the 3770–4000 cm$^{-1}$ range, performing a second comparison with a dried sample, and forming the ratio of the two comparative measurements as a measure of dissolved water content.

18 Claims, 9 Drawing Sheets

MEASUREMENT OF WATER LEVELS IN LIQUID HYDROCARBON MEDIA

BACKGROUND OF THE INVENTION

Several processes in the petrochemical refining industry require information on moisture levels of component streams to optimize the performance of the process or to prevent deterioration of, or damage to, some part of the system. For example, the performance characteristics of chromatographic separation of organic components by adsorbents are affected by the water content of component streams and under dynamic equilibrium conditions there often is a narrow regime of water content within which separation is maximized. The performance of the adsorbents themselves may significantly deteriorate upon water adsorption, or the adsorbents may physically deteriorate at high water levels. Since the processes in question, such as chromatographic separations, often are continuous with the nature of the feed stream time variable, not only is a reliable method of determining water level required, but the method may need to be suitable for frequent periodic use. Although continuous monitoring of water content may be excessive, the monitoring frequency may be relatively high, thereby requiring a short measurement time cycle. Additionally, obtaining individual samples for laboratory analysis is time consuming, inconvenient, and rife with the opportunity of introducing sampling error; methods incorporating on-line measurements are preferable.

Existing water monitors are primarily designed to operate in a gas phase, although two commercially available types are applicable to liquid streams. One type uses a hydrophilic material, usually alumina (although silica or organic polyimides also have been used), placed between two electrodes. As the water level in a liquid stream changes, the hydrophilic material absorbs or loses water, and its impedance change is monitored by means of an AC signal applied across the electrodes. These sensors have three significant disadvantages: the alumina undergoes a shape change when wet causing a permanent offset of the detector when dried arising from the change in the geometry of the material between the electrodes; the sensors are very slow to respond to changes in water composition, especially when the level is low or decreasing; and the sensors do not measure the water concentration directly but instead depend upon the distribution coefficient of water between the organic phase and the hydrophilic layer. As a consequence of the latter, such sensors are very sensitive to any factors which alter the distribution coefficient, such as temperature and, of even greater relevance, the composition of the organic phase. This dependence of the impedance change on the composition of the organic phase makes the measurement of water content only a relative one rather than an absolute measurement. That is, a calibration curve needs to be established for each organic phase whose water level is being determined, an obviously great inconvenience and significant burden.

The second type of commercially available sensor for water in hydrocarbons is based on infrared (IR) absorption by water. These systems generally use the near IR region of the spectrum (1.8–1.9 microns) although some systems are available which use the mid-range (approximately 2.7 microns). In either case, the sensor simply measures the attenuation of IR radiation through the sample of liquid and may also measure a reference attenuation at a wavelength outside the region where water absorbs. This approach also is extremely sensitive to changes in the organic phase since each component of the latter also attenuates the radiation in a characteristic manner. In our studies errors of 200% and more have been observed using the commercial measuring system when the water level was kept constant and only the organic phase was changed.

Our requirements for a suitable measurement method for the detection of water are manifold. One requirement is that the method be insensitive to changes in the organic liquid phase, especially where the latter is a hydrocarbon. The method needs to be capable of determining water level in liquid hydrocarbons at levels as low as about 10 ppm and at least as high as about 1000 ppm. The method is required to be accurate over this range to within 1% or 5 ppm, whichever is greater, and must be reproducible as well. The method needs to be selective for water, especially as to components such as alcohols, amines, and thiols which might be present in the liquid hydrocarbon medium. Finally, the method needs to be adaptable to near-continuous on-line monitoring of process streams.

Several approaches initially were evaluated and discarded because of severe limitations which became apparent in their evaluation, including methods based on microwave absorption, electrochemical measurements, and calorimetric determinations. A modification of the IR approach was considered where the amount of water would be determined by measuring the change in attenuation of IR radiation by a sample compared with the attenuation of the same sample after drying. It was subsequently noted that the absorption spectrum for water in organic liquids consisted of two peaks corresponding to the symmetric and asymmetric OH stretches. More importantly, it was also found that the total area under the two peaks at a given water concentration varied with the nature of the organic phase. However, a chance observation led to the development of the method which is our invention and which satisfies all the stated criteria. In particular, we noticed that as to the water absorption bands in the infrared spectrum of a water-containing homogeneous organic liquid it is only the OH asymmetric stretching frequency which is variable with the organic component, whereas the symmetric stretching frequency is essentially independent of the organic phase, especially when the latter is a liquid hydrocarbon. This observation is the keystone of our invention as described more fully within, and is somewhat contrary to the report of N. M. Alekseeva and E. E. Yudovich, *Zhurnal Prikladnoi Spektroskopii*, 15, No. 6, 1076–9 (1971), which indicates that the ratio of intensities of the symmetric and antisymmetric stretching bands remain constant with changes in solvent. The authors recommend use of the antisymmetric stretching band in water measurements in contradistinction to the method used in this invention.

Although one aspect of our invention is a method of measuring water concentration in a liquid hydrocarbon where the method is essentially independent of the hydrocarbon, in another aspect our invention is an online instrument to measure water in hydrocarbons in an automated, maintenance-free manner. The relative invariance of the symmetric stretching frequency of the water molecule provides the key to successfully effecting our invention.

SUMMARY OF THE INVENTION

The purpose of our invention is to provide a method of measuring the dissolved water content in a liquid organic phase, especially a liquid hydrocarbon, at levels from at least about 10 ppm up to the saturation level of water in the liquid hydrocarbon, which may be at least as high as about 1000 ppm. In one aspect our invention is a method of determining the water content by measuring the attenuation of light at the infrared symmetric OH stretching frequency of water over a narrow wavelength interval. A second aspect of our invention is an apparatus which quickly, accurately, selectively and reproducibly measures the amount of dissolved water over about 10 ppm up to the saturation level of water in the liquid organic phase, where said measurement is independent of the liquid organic phase in which the water is dissolved. Other embodiments will be apparent from the ensuing description.

DESCRIPTION OF THE FIGURES

FIG. 2 shows positions for withdrawal of the sample from the stream into the reservoir. FIG. 3 shows valving when sample is passed into a column of molecular sieve for drying and then into the cell, and FIG. 4 shows positions for direct injection of the sample stream into the cell.

DESCRIPTION OF THE INVENTION

Figure 1:
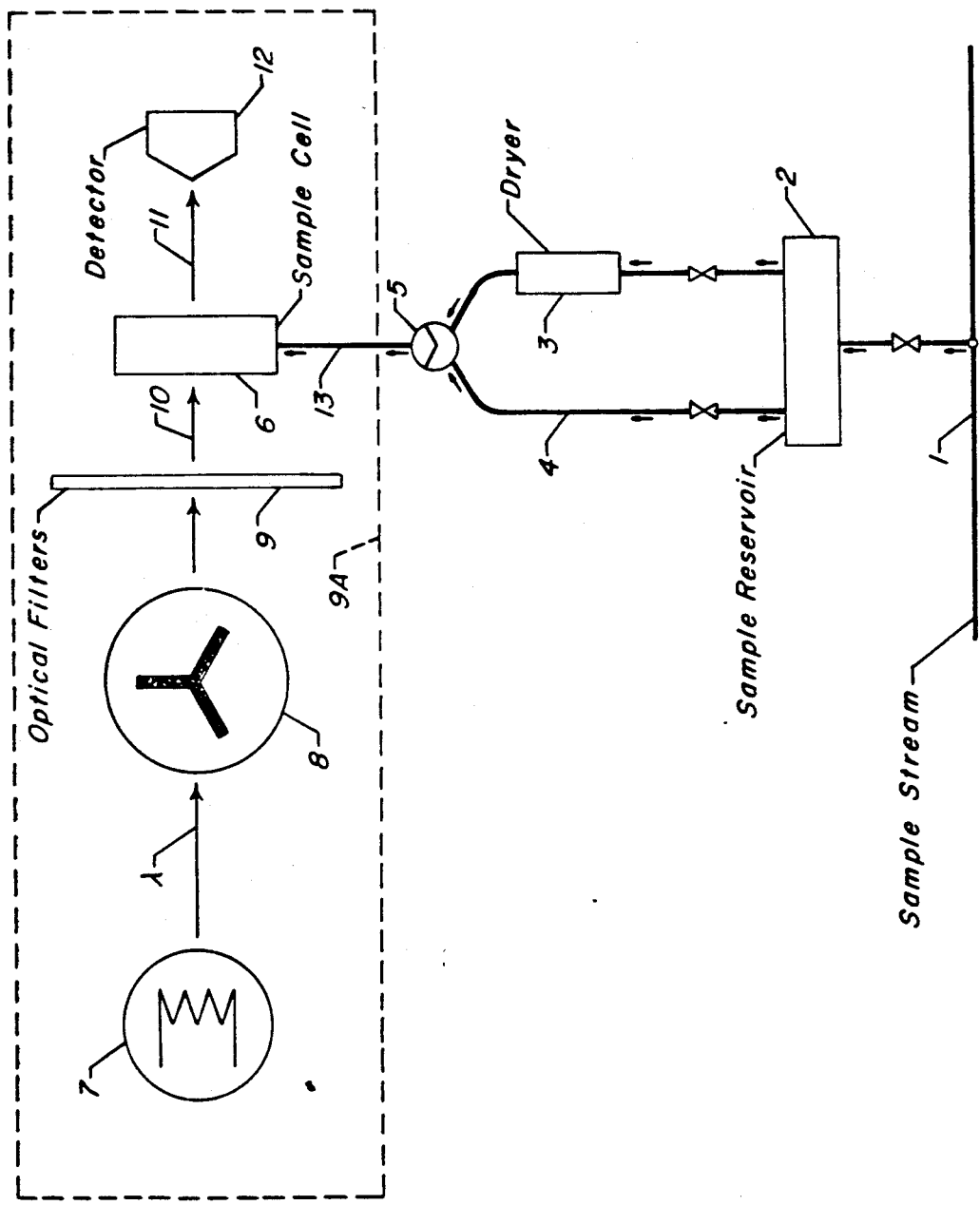
FIG. 1 is a diagram showing both a generalized sampling process and an infrared measuring apparatus for the determination of water in organic liquids.

As stated previously, our method affords the measurement of water in many liquid organic phases with high selectivity, accuracy, and reproducibility, and does so quickly over a wide range of water content. When the liquid is a hydrocarbon, our method has the important and outstanding feature of being relatively independent of the hydrocarbon in which the water is dissolved, making it applicable to a broad range of liquid hydrocarbons. Although liquid hydrocarbons constitute an important class of organic liquids for which our invention is operable, it is not meant to imply that hydrocarbons are the only such class. The main requirement which an organic liquid must satisfy for our method to be applicable is that it not effect a non-linear concentration-dependent distortion of the symmetric hydroxyl stretching frequency of dissolved water. Even if our subsequent exposition is couched in terms of liquid hydrocarbons, it is to be understood that this is solely for convenience, and is not intended to restrict the scope of our invention.

The method which is our invention is suitable for measurement of water in an organic liquid phase where the water concentration is 10 ppm or more. Although the method in principle may be used for measurement of water at concentrations under about 10 ppm, it is found that satisfactory accuracy and precision sets a reasonable lower limit of about 10 ppm water. The method is applicable to measurements of water at concentrations up to the saturation level of water in the liquid organic phase. We are not aware of any fundamental limitations imposed by our method on the maximum water concentration which can be measured; water concentrations of 1000 ppm can be measured accurately and precisely be our method, and substantially higher concentrations could be expected to be amenable to measurement by our invention.

Our invention may be briefly stated as follows. The attenuated infrared radiation intensity for an organic liquid phase containing dissolved water is measured within the interval of 3490–3690 $cm^{-1}$ using a narrow bandwidth filter. The attenuation which we measure arises largely from that of the hydroxyl symmetric stretching mode of water, but contains a contribution from the organic phase itself. To compensate for the IR radiation absorbed by the organic phase, and to compensate for non-chemical sources of IR attenuation (e.g., dirt particles and air bubbles), the intensity of transmitted light of the organic liquid phase containing dissolved water is measured at a nearby region of the infrared spectrum where there is little or no attenuation arising from water absorption and where the liquid organic phase is relatively transparent. The ratio of these two transmitted light intensity measurements is then the relative transmittance arising from dissolved water in the liquid organic phase. A portion of the same sample of liquid organic phase containing dissolved water is also dried by suitable drying means, and a similar set of transmitted light intensity measurements is made on the dried liquid organic phase to give a relative transmittance for the dried sample. The difference between the corrected transmittances for the wet and dried samples is then a direct measure of water content in the organic liquid. This method is elaborated upon more fully within.

As we describe below, the method may be fully automated and incorporated in an apparatus which is another aspect of our invention. Automation may be achieved via a hard wired control system, which offers invariance and freedom from operator variation, or it may be under software control, which is more elaborate but also may be much more flexible. Whatever the particular configuration of the control system it may be designed to compensate for external variables which may influence the result such as differences in temperature and other variables having a significant effect on the outcome of the measurements. The automation system may include periodic withdrawal of samples at predetermined times, directing a portion of the wet sample to the measuring instrument and a second portion of the wet sample to the drying means, determining the transmittance of the sample coming from the drying means, or more properly a signal which is a measure of the transmittance, exchanging the dried sample with an undried sample, obtaining a second set of transmittance determinations on the undried sample, and then performing the necessary conversions to obtain from the measured transmittances a direct reading of the water dissolved in the liquid organic phase.

Although the method of our invention is applicable to the measurement of dissolved water in many different liquid organic phases, it is particularly pertinent to liquid hydrocarbons. The measurement may be applied to any liquid organic phase so long as the latter does not interfere with the symmetric stretching frequency of water in the infrared spectrum. The interference which causes the most complications arises when the organic liquid changes the symmetric stretching frequency of water (vide supra) because of, for example, interaction between water and the organic phase, such as weak hydrogen bond formation. In this context the suitability of the use of a polar organic material as the liquid phase must be individually determined, but this determination requires nothing more than routine screening of the solvent containing varying small levels of water. Yet another situation where the organic phase may be unsuitable arises when the latter contains other interfering substances, such as secondary components in the organic phase as exemplified by amines, alcohols, and so on. In this situation the secondary components may form hydrogen bonds with the water, causing distortion of the symmetric stretching frequency spectrum which interferes with the measurement of the water, or the secondary components may associate with dissolved water to shift its symmetric stretching frequency.

Although the foregoing kinds of interference complicate application of our invention, nonetheless both our method and the instrumentation developed to practice our method remain useful but may require the experimental determination of a set of calibration standards for each particular water-organic liquid system. It also should be mentioned that non-linearity may result from self-association of water at higher concentrations, which may necessitate incorporation of a non-linear equation of fit.

The following description is of a method where transmitted light intensity measurements are first made on a dried portion of the sample followed by transmitted light intensity measurements on an undried sample. Although we prefer this sequence in carrying out our invention and believe it is operationally advantageous, this is not to say that this sequence is mandatory, or that the success of our invention is dependent on the sequence. It may well be that with careful operating technique a sequence different from that in our description will be at least as convenient and reliable; nonetheless, our current preference is reflected in the following description.

A portion of the liquid organic phase containing dissolved water is dried. Any suitable drying means may be used so long as it meets the requirements of being unreactive with the organic phase, it does not itself cause absorption in the infrared which would interfere with the measurements performed at the IR wavelength used (vide infra), and it removes water from the liquid organic phase down to a level of at least 1 ppm. Among the drying means which may be mentioned are included the use of high surface area sodium, the use of active metal turnings in general, passage of the liquid through a column of an inorganic oxide such as sodium oxide, barium oxide, and phosphorus pentoxide, and the use of molecular sieves. The latter are particularly attractive because sieves may be chosen which are quite selective for water absorption, because drying to the indicated water level is readily attainable, because molecular sieves can be easily regenerated for multiple use and because of their safety, reliability, and ease of use. It is also possible to have but a single drying means or multiple drying means, so that, for example, some of the drying means may be in a regenerative mode at the same time that others are in the absorption mode. The particular molecular sieve employed is not an especially critical factor so long as it selectively removes water from the liquid organic phase to a level of at least 1 ppm. A hydrophilic molecular sieve having pore diameters small enough to exclude most of the molecular species of the organic phase while including water is preferred. Examples include zeolites 3A, 4A, and 5A, and a comprehensive listing of suitable materials may be found in "Zeolite Molecular Sieves", D. W. Breck, J. Wiley and Sons, New York (1974).

The intensity of light transmitted through a known path length of the dried liquid organic phase is measured at 3590 $cm^{-1}$ (2.7855 microns), which corresponds to the frequency of the symmetric stretching mode of water in the infrared. We have found that the frequency of the symmetric stretching mode is effectively independent of the nature of the liquid hydrocarbon phase so long as there is no interference, as discussed above. To further ensure accuracy of the method as well as independence of the method on the nature of the liquid hydrocarbon, transmitted light intensity measurements are made using as narrow a bandwidth filter as feasible so that the light incident on the sample is largely, and most preferably exclusively, within the envelope of the absorption arising from the symmetric stretching mode of water in liquid hydrocarbons, which spans the range of about 3540-3640 $cm^{-1}$. Measurements utilizing transmitted light having components with a wavelength in the 3640-3690 $cm^{-1}$ (2.7473-2.7100$\mu$) region encompass some of the asymmetric stretching mode absorption envelope, and consequently show some dependence on the nature of the liquid hydrocarbon, but nonetheless often afford sufficiently accurate results to be usable. The operational conclusion to be reached is that although a narrow bandwidth filter passing light in the 3490-3690 $cm^{-1}$ (2.8653-2.7100 $\mu$) region may be used so long as the transmitted light intensity arises largely from components of wavelength under 3640 $cm^{-1}$, it is preferable to use a filter whose bandwidth is in the 3540-3640 $cm^{-1}$ region.

In order to correct the foregoing intensity reading for non-chemical sources of attenuation, a second measurement is made with another narrow bandwidth filter in a similar region of the infrared spectrum which is, however, just outside that of the OH stretching frequencies of water, preferably in a region where the liquid organic phase is relatively transparent (i.e., high transmission, low absorption) and where the absorption due to water is negligible. The range, or bandwidth, of this interval over which measurements are determined is desirably as narrow as possible, preferably 150 $cm^{-1}$ or less, more desirably 100 $cm^{-1}$ or less, optimally no more than 70 $cm^{-1}$. We have chosen the region in which this second measurement is made as 3770 to about 4000 $cm^{-1}$ (2.65-2.5 $\mu$). The ratio of these two measured transmitted light intensities is then referred to as a relative transmittance. We emphasize that this second measurement affords a baseline absorption which we have determined to be a significant and convenient correction to the water absorption; although we have chosen the 3770-4000 $cm^{-1}$ region, we do not claim it is unique, and other regions in the IR may be chosen where these are more convenient or advantageous.

Transmitted light intensity measurements are then made on the wet (untreated) liquid organic phase in the same manner as was done for the dried liquid organic phase. In particular, a relative transmittance is determined as described above. The difference between the corrected relative transmittance obtained for the wet sample and that obtained for the dried sample is a measure of the water dissolved in the liquid organic phase.

More particularly, it is the difference in the logarithms of the relative transmittances which is used as the measure of water content. One skilled in the art will recognize that the logarithm of the reciprocal of transmittance is absorbance, and it is the difference in relative absorbances which is used as the measure of water content. It often is highly desirable to construct a calibration curve, i.e., to experimentally determine the relation between the absorbance differenc as described above and the water content of the liquid organic phase as determined, for example, by Karl Fisher titration, in order to obtain a relationship between the two methods. As expected from Beer's law, usually there is a linear relation between the difference in absorbance as described above and the water content as determined via Karl Fisher titration, but some curvature may arise from the various interactions described above in the context of interfering factors. In any event, such calibration curves enhance the accuracy of our method and are highly recommended.

FIG. 1 is a diagram showing the process of sampling a liquid organic stream and determining its water content according to the practice of our invention. The wet organic phase whose water content is to be measured is designated as stream 1, a portion of which is periodically withdrawn into a sample reservoir, 2. Periodically an amount of the wet organic phase in the sample reservoir is metered to a dryer, 3, containing drying means. The wet organic phase remains in contact with the drying means for a time adequate to remove water from the organic liquid to a level not more than about 1 ppm. After a time sufficient to lower the water content to not more than 1 ppm, at least a portion of the dried liquid organic phase is directed to an infrared sample cell, 6, via valve 5.

The upper portion of the figure within the dotted lines represents the infrared apparatus used in our measuring system. Light source, 7, provides broad spectrum radiation subject to the requirements of stability and sufficient intensity at the measuring infrared frequencies as to provide adequate signal to noise ratio. We have found it necessary to carefully control lamp voltage by incorporating the lamp voltage supply in a feedback circuit in order to have an infrared beam intensity showing excellent stability with respect to short term fluctuations. For the measuring frequencies we prefer, the source must at least provide radiation in the 3400–4000 cm$^{-1}$ range (2.94–2.50 microns). Suitable sources are well known to practitioners of infrared spectroscopy and include a simple incandescent tungsten bulb, tungsten-krypton and tungsten-halogen bulbs, and a Nernst glower. Radiation emitted from the light source is then converted into pulsed radiation by chopping means, 8. A means for converting a steady radiation source into pulsed radiation is exemplified by a disk mounted between the light source and sample cell, 6, having one or more openings for passage of light and rotating at a constant frequency. Light then passes through the disk at intervals determined by the number of openings on the disk and the rate at which the disk rotates. Although this is the preferred method of providing chopped light, chopping also can be achieved using electrooptic shutters or vibrating reed systems. For our method, we have found a chopping frequency of 320 to about 450 Hz to be quite desirable. However convenient and beneficial this particular frequency range may be to the particular manner in which we practice our invention, it may well be that another range may be preferable to other specific modes of practicing the invention, depending, e.g., on the electronic circuits employed. Close control of the chopping frequency appreciably increases the precision achieved in the measurements, and a frequency constant to ±0.1 Hz has been found quite beneficial. Where the chopper is a disk rotated by a motor, a speed control for the motor to achieve the frequency stability sought is a virtual necessity.

An optical filter, 9, is placed between the means for chopping the IR radiation and sample cell in order to ensure that light incident on the sample cell is within the appropriate narrow wavelength range. It needs to be noted that although the filter usually will be placed between the chopping means and sample cell, it may be placed between the light source and chopping means, especially if provision is made to avoid any stray light being incident upon the sample cell. The optical filter also may be placed after the cell and before the detector, although the need to avoid stray light being incident upon the detector is an even greater consideration in this case.

Although only one filter at a time is interposed in the light path between the radiation source and sample cell, two filters are actually employed in our method of determining the water content of a liquid organic phase. As previously stated, one filter (sample filter) is a narrow bandwidth filter providing incident radiation in the interval of 3490–3690 cm$^{-1}$ and is used during the measurement of the IR radiation transmitted at the frequency of the symmetric stretching mode of water. The other filter (reference filter) is also a narrow bandwidth filter providing incident radiation in the range of 3770–4000 cm$^{-1}$ and is used during the determination of baseline IR transmission of the organic liquid phase. These filters are alternately switched in and out of the light path as needed for infrared measurements by a swapping means, 9A, which is not otherwise shown in the diagram. A convenient method of switching the filters in the incident light path is using an appropriate motor/cam combination to impart a linear motion to a filter holder having the reference filter mounted in one half and the sample filter mounted in the other half. Alternatively, a filter wheel could be used with the two (or more) filters mounted on a rotating wheel and alternately rotated into the light path. These are certainly only exemplary of the swapping means which can be used rather than being exhaustive in nature. What is important to understand is that one and only one of these filters is in the light path at all times during absorption measurements, as described more fully below.

The wet or dried sample of organic liquid is placed in a sample cell, 6, which receives chopped and filtered incident light, 10. The intensity of the light transmitted through the sample, 11, is then determined by a lead sulfide detector, 12, having a thermoelectric cooler to increase its sensitivity. We have found a lead sulfide detector to be particularly appropriate for our measurements, although other photoconductive (GeCd and PbSe), photovoltaic (InAs and InSb), or various thermal detectors (thermopile, pyroelectric, or thermistor bolometers) also could be used. Whichever detector is used, it serves as a transducer and generates an electrical signal proportional to the incident infrared radiation at its surface. The detector is so aligned as to be in the light path coming from the source through the chopping means and filters and through the sample cell. It should be clear that the only infrared radiation incident on the detector is that transmitted through the sample cell. The detector signal is then amplified by means well known in the art and which need no further discussion. However, a variant which we have found particularly valuable is that of an operational amplifier in combination with a narrow bandpass filter to provide an amplified signal at the frequency of the chopper motor. This variant selectively amplifies only signals at the chopper motor frequency and affords a substantial signal-to-noise ratio increase.

The radiation intensity of light transmitted through the infrared cell filled with dried organic liquid phase is determined within a first frequency interval of about 3490 to about 3690 cm$^{-1}$ using the appropriate optical filter. This filter is then replaced with the second filter which passes radiation in another portion of the infrared spectrum relatively transparent to water absorption. We have found the region of 3770 to about 4000 cm$^{-1}$ to be a very convenient second frequency interval for the second transmittance measurement, and filters with bandwidths of no more than 150 wave numbers are preferred, no more than about 100 wave numbers still more preferred, and filters with a bandwidth of no more than about 70 wave numbers optimal. A second transmitted light intensity is then measured at the second frequency interval, and the ratio of the first and second transmissions through the dried liquid is taken to afford a first relative transmittance.

As a matter of technique, the intensity of light transmitted through the sample cell is checked for signal stability by obtaining three 3-point averages. If the signal is unstable, at least a portion of the liquid in the sample cell is replaced by fresh stock from the dryer. This is repeated until a stable signal is obtained, at which time the transmitted light intensity is measured for transmittance determination by averaging 50 separate readings.

When transmittance determinations on the sample cell containing the dried portion of the liquid organic phase are complete, the contents of the infrared cell are replaced with a portion of the wet liquid in the sample reservoir via the line 4 and 3-way valve 5. Again as a matter of technique, the cell is generally flushed with a dry gas such as nitrogen prior to injection of a wet sample, and then flooded with a sufficient amount of wet sample so as to ensure no significant error arising from residual dried organic liquid in the sample cell. With the wet organic liquid in the sample cell, the same measurements as were performed on the dried sample are taken once more. Thus, the transmitted light intensity is checked for signal stability by taking three 3-point averages and replacing the sample cell contents with fresh wet organic liquid until a stable signal is observed. Once signal stability is attained, 50 readings are taken within a first interval of about 3490 to about 3690 cm$^{-1}$, followed by a like number of readings using light transmitted by the second filter in the range of, for example, 3770 to 4000 cm$^{-1}$. The ratio is taken to obtain a second relative transmittance, and the difference between the first and second absorbances (i.e., the logarithm of transmittance) measured as described above is proportional to the water content in the sample.

Figure 2:
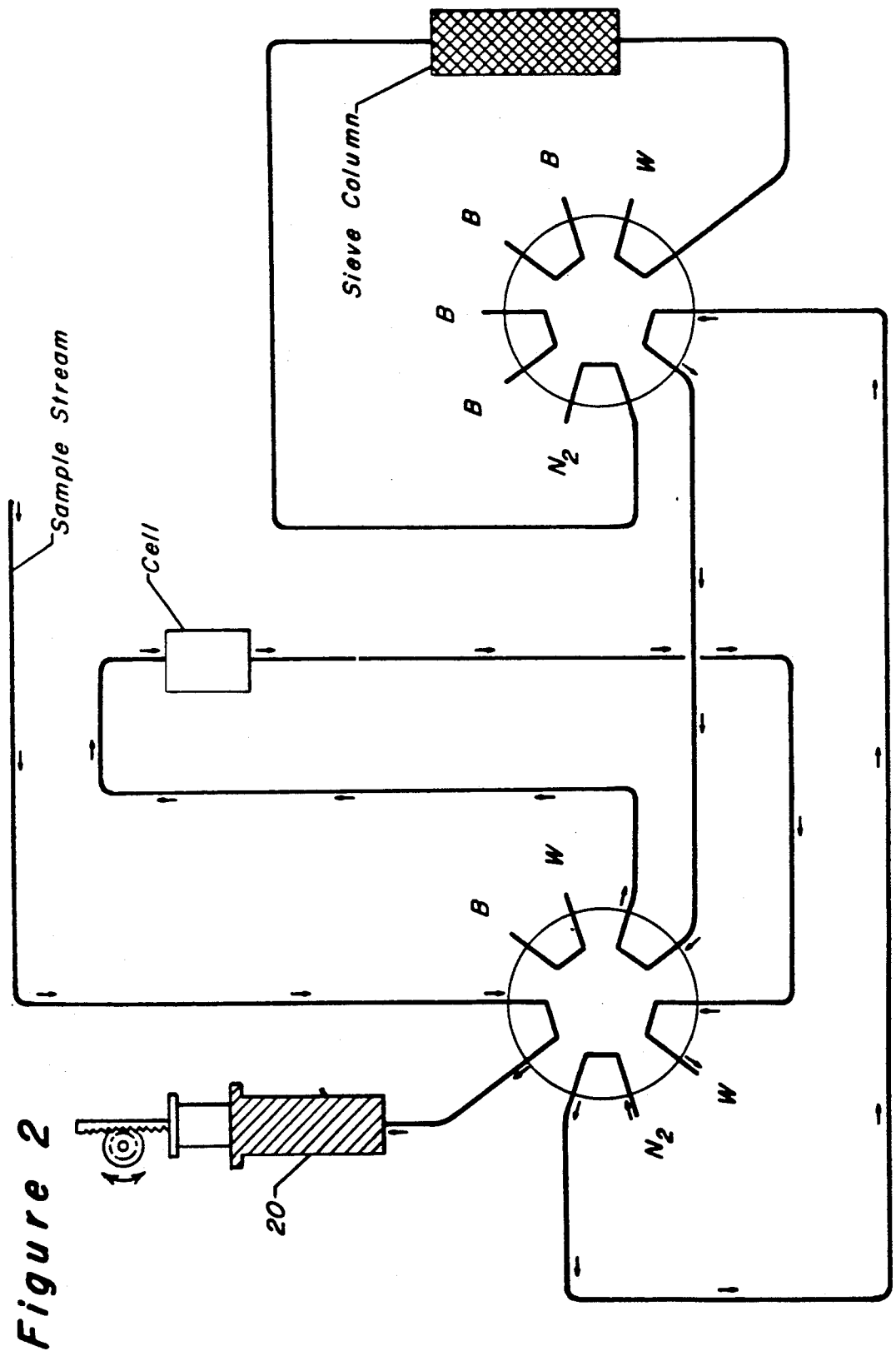
FIGS. 2–4 are diagrams of a more particularized sampling process showing different valve positions and liquid flows.
Figure 3:
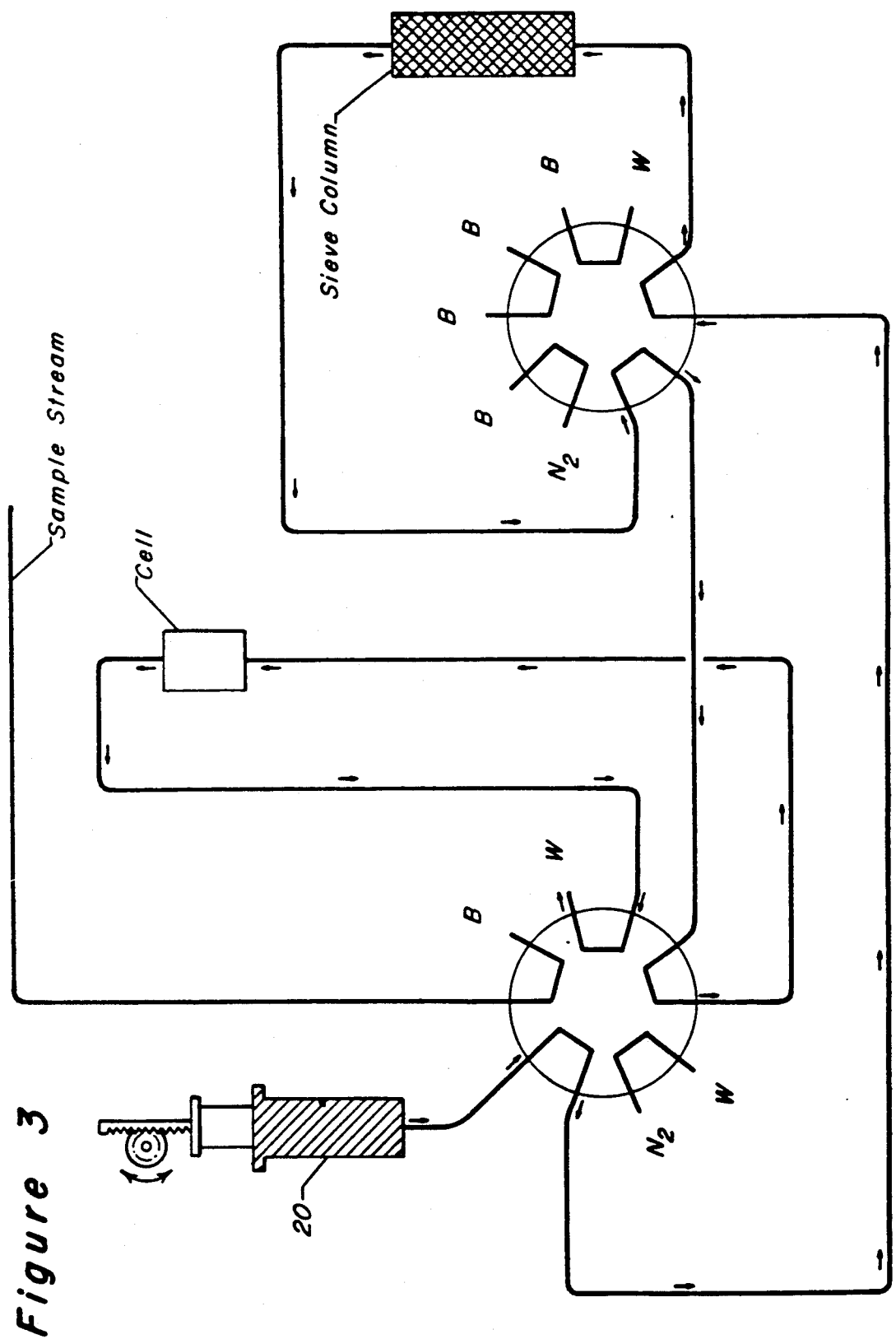
Figure 4:
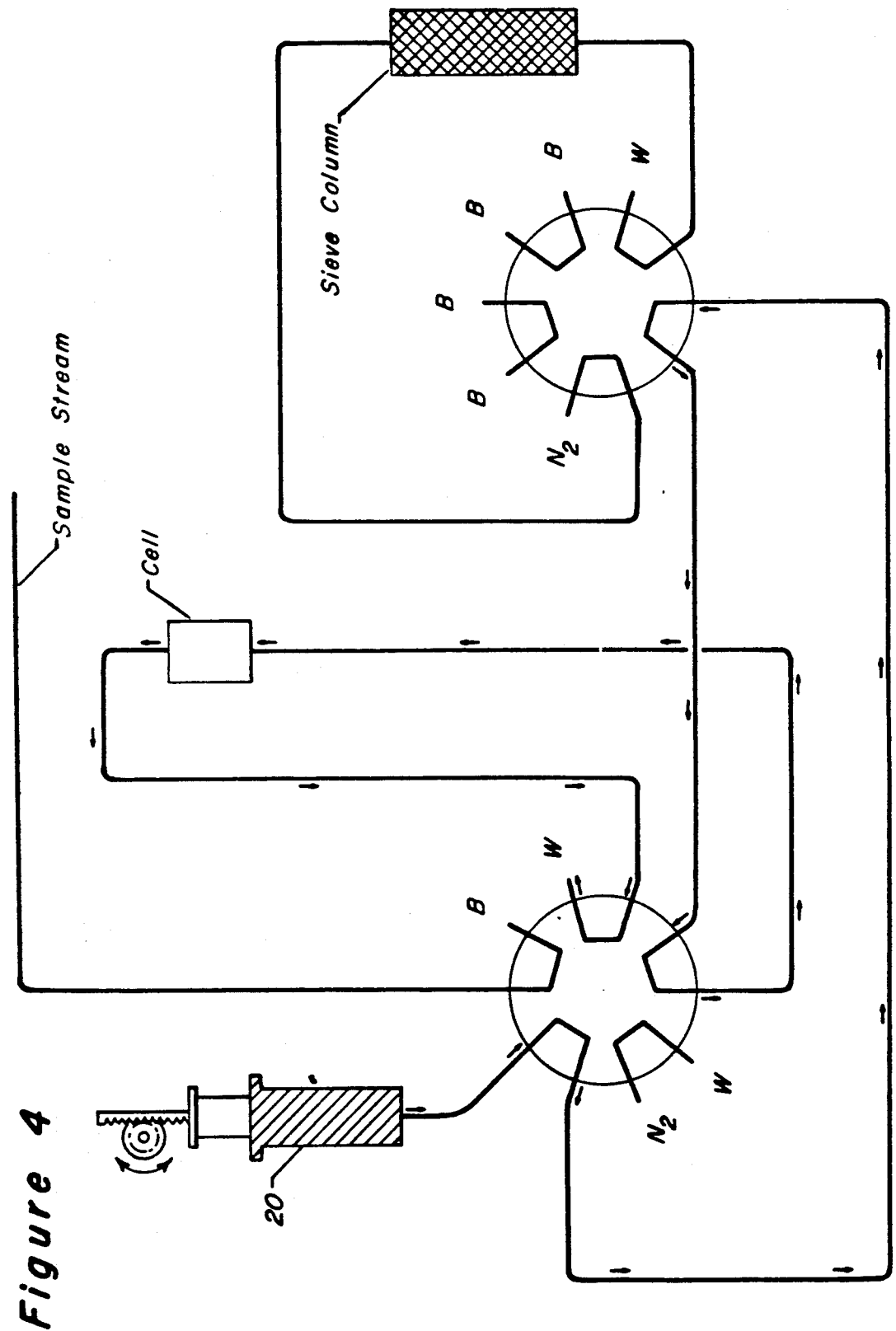

FIGS. 2-4 show a sampling system which we have found particularly convenient. A sampling syringe, 20, serves as the sample reservoir and has a barrel or plunger which is under precise computer control so that reproducibly exact amounts of liquid can be metered. In the position shown in FIG. 2, a portion of the process stream is withdrawn into the sampling syringe while both the sample cell and dryer are being purged with a dry gas, such as nitrogen. In the valve position shown in FIG. 3, a precise and predetermined amount of wet liquid is sent to the dryer. After a contact time sufficient to reduce the water content in the wet organic liquid to no more than 1 ppm, metering of additional liquid from the sampling syringe forces a portion of the dried organic liquid into the infrared cell, where light transmission measurements of the dried liquid can be obtained.

After transmission measurements on the dried liquid are complete, FIG. 4 shows the next position of the valves. Here wet liquid may be metered directly from the sampling syringe into the infrared cell. At the same time the dryer is purged with a dry gas, such as nitrogen, so as to remove all traces of the organic liquid within the dryer. The dryer should also be heated to assist removal of water absorbed by the drying means as well as the last traces of organic liquid in the dryer. After IR transmission measurements are complete on the wet sample, the valves are switched back to the positions shown in FIG. 2 prior to the next sampling cycle.

The following are non-limiting examples of some aspects of our method. Suitable variations and extensions will be apparent to the skilled artisan and are intended to be encompassed within our invention.

General Procedure

A sample is automatically drawn into a holding reservoir from a process stream to be analyzed using an automated syringe. A first portion (8 mL) of the sample in the reservoir is injected into a 10-mL column of a 4A molecular sieve (although a 3A sieve also could be used) and allowed to dry for a predetermined period of time. There was no appreciable difference in results using drying times ranging from 10 seconds to 10 minutes, and a drying time of 3 minutes was chosen to minimize bubble formation in the column due to local heating. The dried sample was then injected into the infrared cell by moving an additional 6 mL from the reservoir into the drying column. The transmitted infrared intensity was measured using first the sample (water peak) filter, the reference filter was automatically switched into place at the end of the sample readings, and a second set of reference measurements were made. The cell then was automatically flushed with dry nitrogen and a portion of the undried sample from the reservoir was injected into the cell. Two readings again were taken using the sample and reference filters as described above. Finally, the cell was purged with nitrogen and the molecular sieve column was automatically heated to about 110° C. and purged with dry nitrogen to regenerate the sieve between samples. At this point a new cycle is ready to begin. A measurement cycle of 3 minutes plus a 3-minute residence time in the molecular sieve column was found convenient to use.

Before the measured infrared intensity was stored, the signal was analyzed for long- and short-term instability and a second or third sample was injected where necessary. The retained readings were an average of 50 individual measurements, and these averaged readings were used to compute the water concentration. The instrument was calibrated with a solution containing a known amount of water and the resulting calibration constant was stored for use in converting the measured signals for unknown samples to their corresponding water concentration. Data output from the software program included the sample and reference voltage readings for the dried and undried samples, the sample/reference voltage ratios for each, and either the calibration constant or the water concentration of the sample, depending on whether the measurement was carried out in calibration- or analysis-mode. The water concentration (or calibration constant) was determined from the measured intensities using the equation, $$[H_2O] = K \cdot \log(R_d/R_w)$$

where $R$ = (intensity through sample filter)/(intensity through reference filter) and $d$ and $w$ refer to dry and wet samples respectively, and K is the calibration constant. If the instrument contained an electronic offset (i.e., a non-zero signal when no light was incident upon the detector), this was first subtracted from the measured intensities before the ratios were calculated.

EXAMPLE 1

Measurements Including Contributions From Asymmetric Stretching Mode

Figure 5:
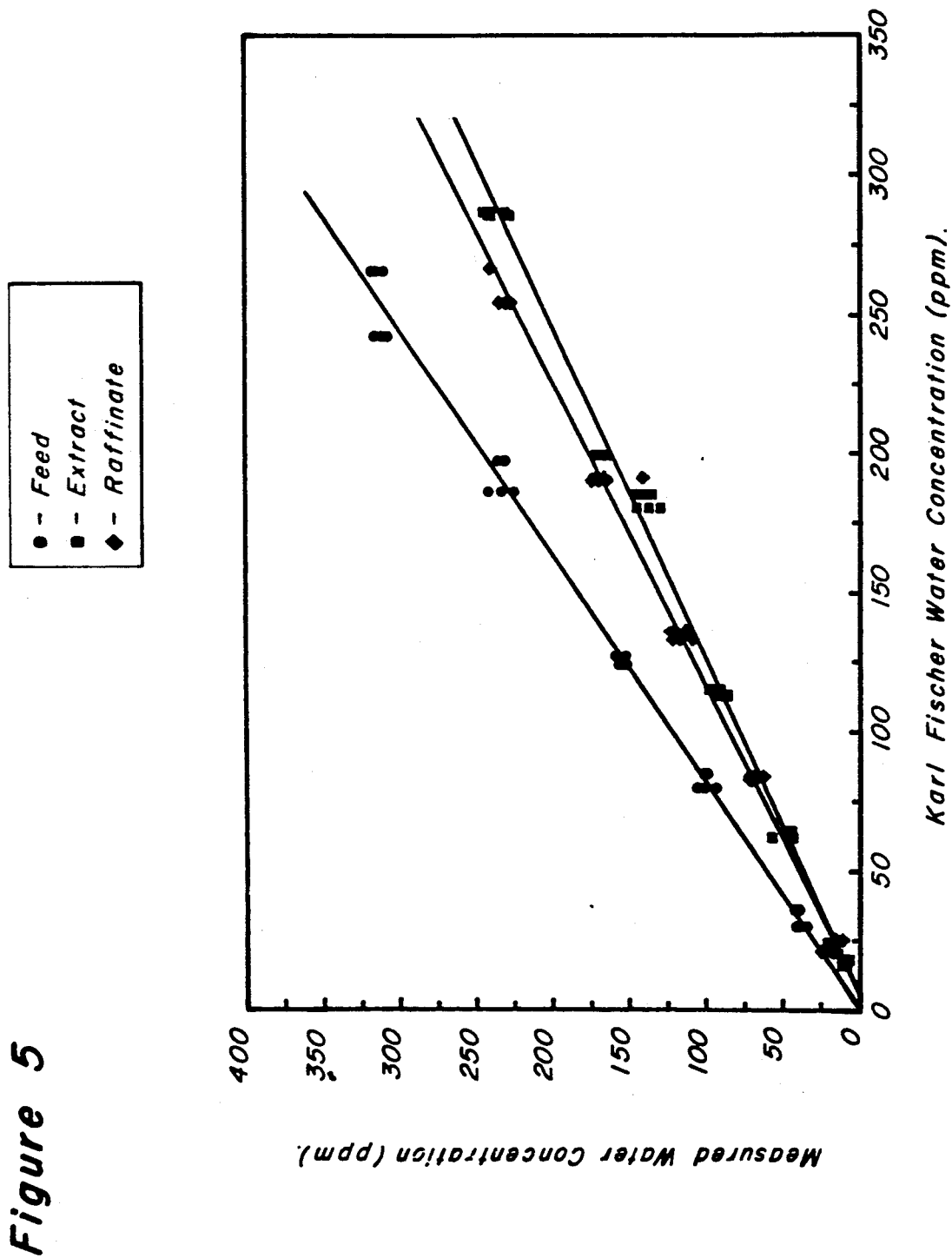
FIG. 5 is a graphic showing the correlation between water content as measured by the Karl Fischer method and our infrared method using a sample filter passing frequencies for both the symmetric and asymmetric stretching modes of water.

Measurement of the water concentration was made using the aforedescribed general procedure on 1) a feedstock consisting primarily of a mixture of xylenes and ethyl benzene, 2) a para-xylene enriched extract from this feedstock resulting from chromatographic separation, and 3) raffinate from the feedstock resulting from the same separation. The reference wavelength was determined by an optical filter passing radiation centered at 2580 nanometers with a bandwidth of 50 nanometers (3839-3914 cm$^{-1}$). The sample filter wavelength was centered at 2780 nanometers with a bandwidth of 200 nanometers (3472-3731 cm$^{-1}$). Water concentration determinations were made on the same samples using the Karl Fisher method. The correlation between results using infrared and Karl Fisher methods are portrayed in FIG. 5. It can be readily seen from the figure that a good correlation between the infrared and Karl Fisher methods was present for both the feedstock, raffinate, and extract. It is equally clear that each of these streams falls on a separate line.

Figure 6:
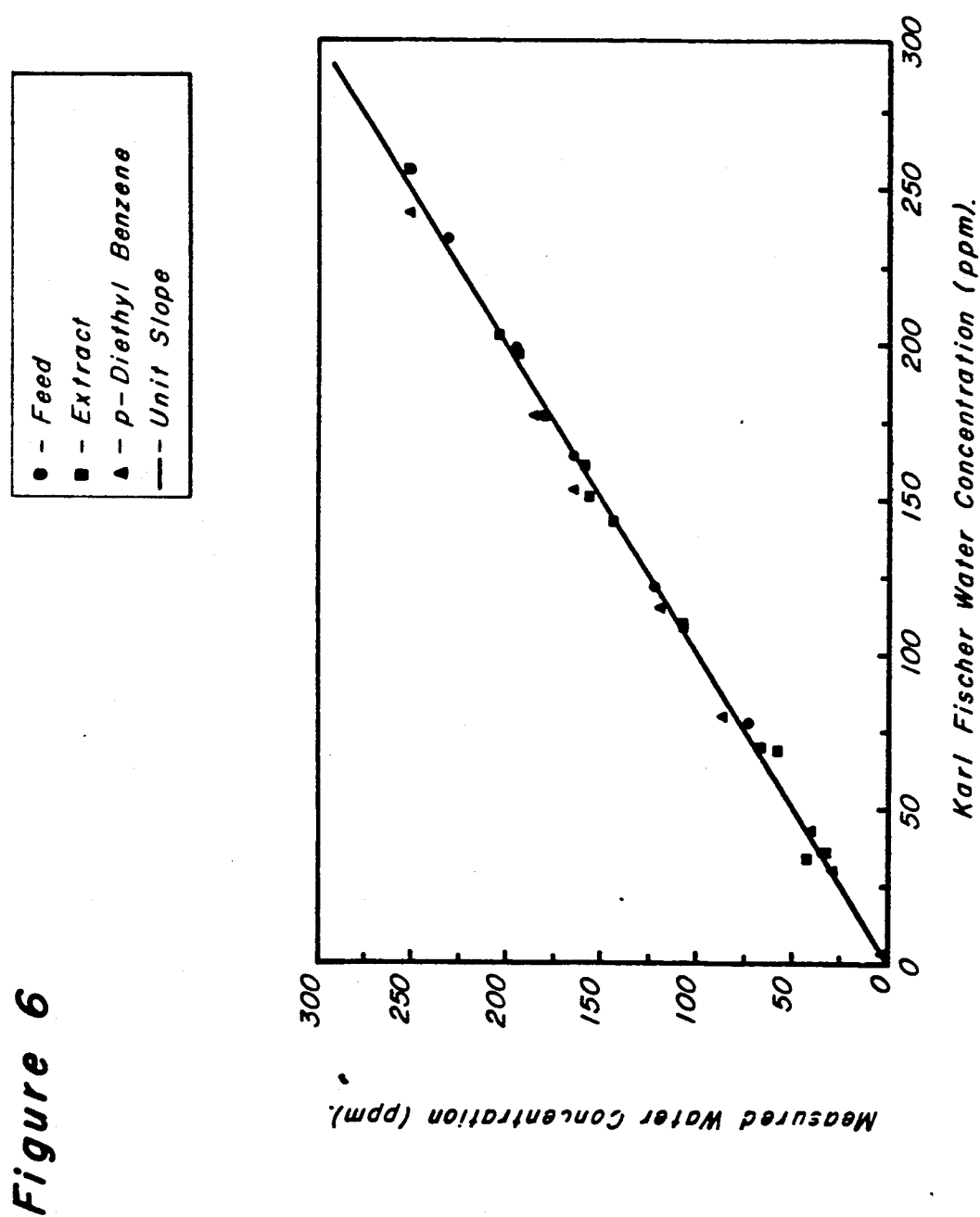
FIG. 6 is a graph showing the analogous correlation when the sample filter passes only frequencies for the symmetric stretching mode.

That there are 3 separate and distinct linear correlations arises from the fact that the sample filter passes wavelengths which encompass the frequency of both the symmetric and asymmetric stretching modes of water. This was clearly shown when the sample filter was replaced with one whose wavelength maximum was 2795 nanometers having a bandwidth of only 55 nanometers (3543-3613 cm$^{-1}$), which corresponds to measurements using the peak arising from the symmetric stretching mode only. These results are shown in FIG. 6, where the points from the feedstock, extract, and raffinate lie on the same line.

EXAMPLE 2

Figure 7:
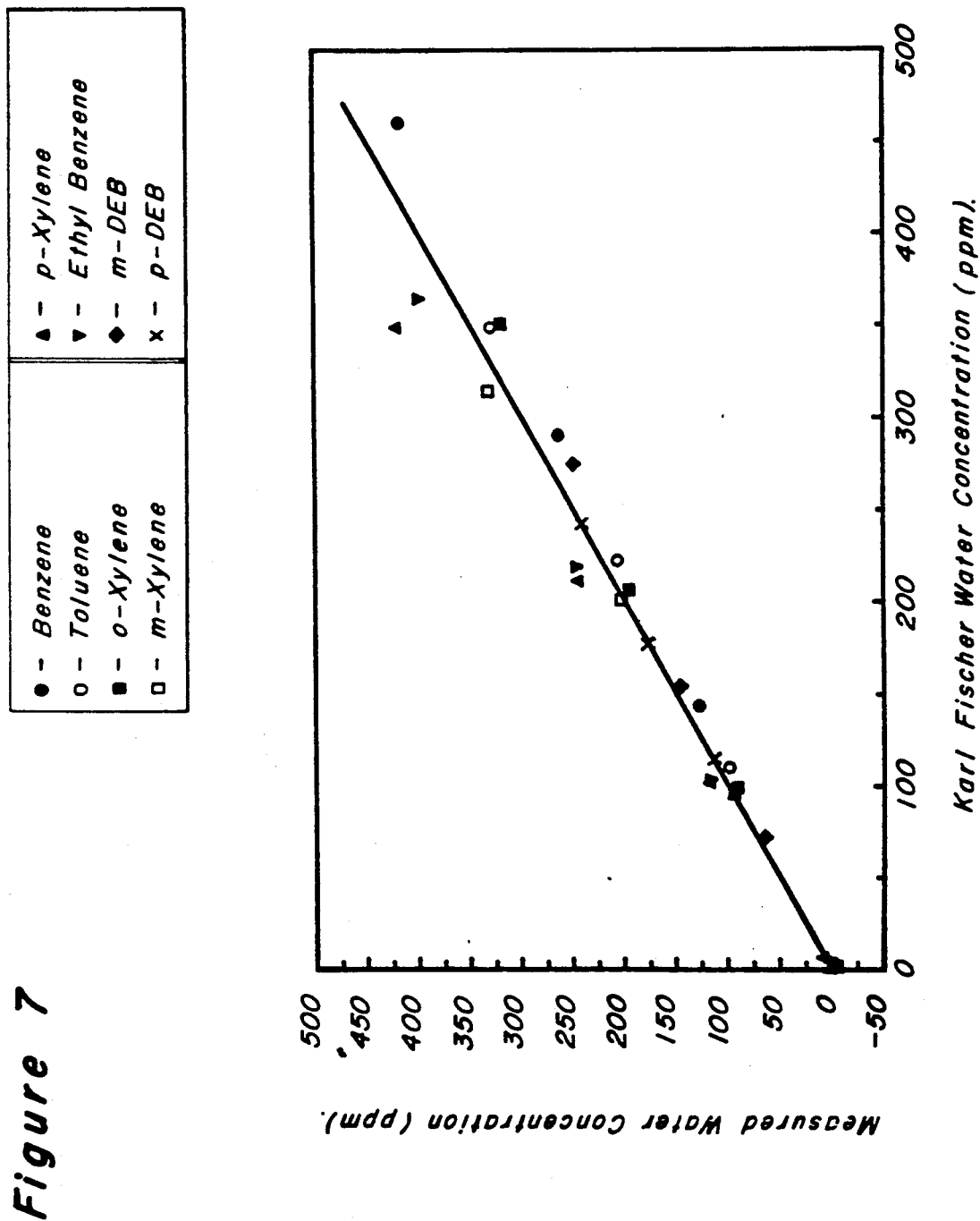
FIG. 7 shows the invariance of water concentration measurements with solvent using the symmetric stretching peak only.

Invariance of Water Concentration Measurements with Solvents Using Symmetric Stretching Peak Only Water measurements were made using both the infrared and Karl Fisher methods in several aromatic hydrocarbons. Results for benzene, meta-diethylbenzene, para-diethylbenzene, ethylbenzene, orthoxylene, meta-xylene, and para-xylene are shown in FIG. 7. That all the points fall on the same straight line demonstrates that when only measurements using the symmetric stretching frequencies are utilized the results are relatively independent of the liquid hydrocarbon used as a solvent. When a sample filter is used which passes both the symmetric and asymmetric stretching frequencies, the scatter in measurement results is appreciable and requires a separate correlation for each solvent.

EXAMPLE 3

Effect of Active Filter

Figure 8:
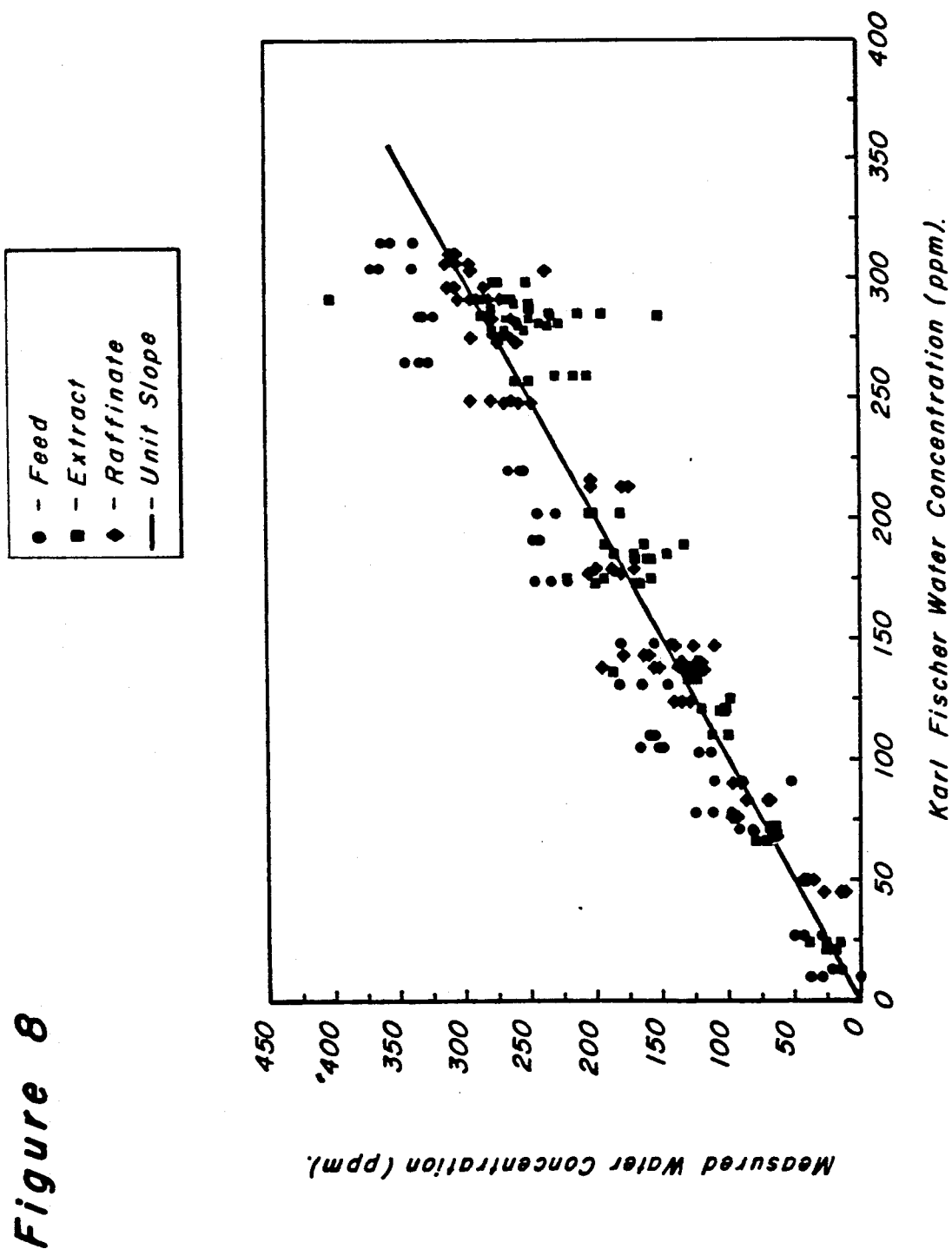
FIGS. 8 and 9 depict the scatter in measurements without an active filter (FIG. 8) and with an active filter (FIG. 9).
Figure 9:
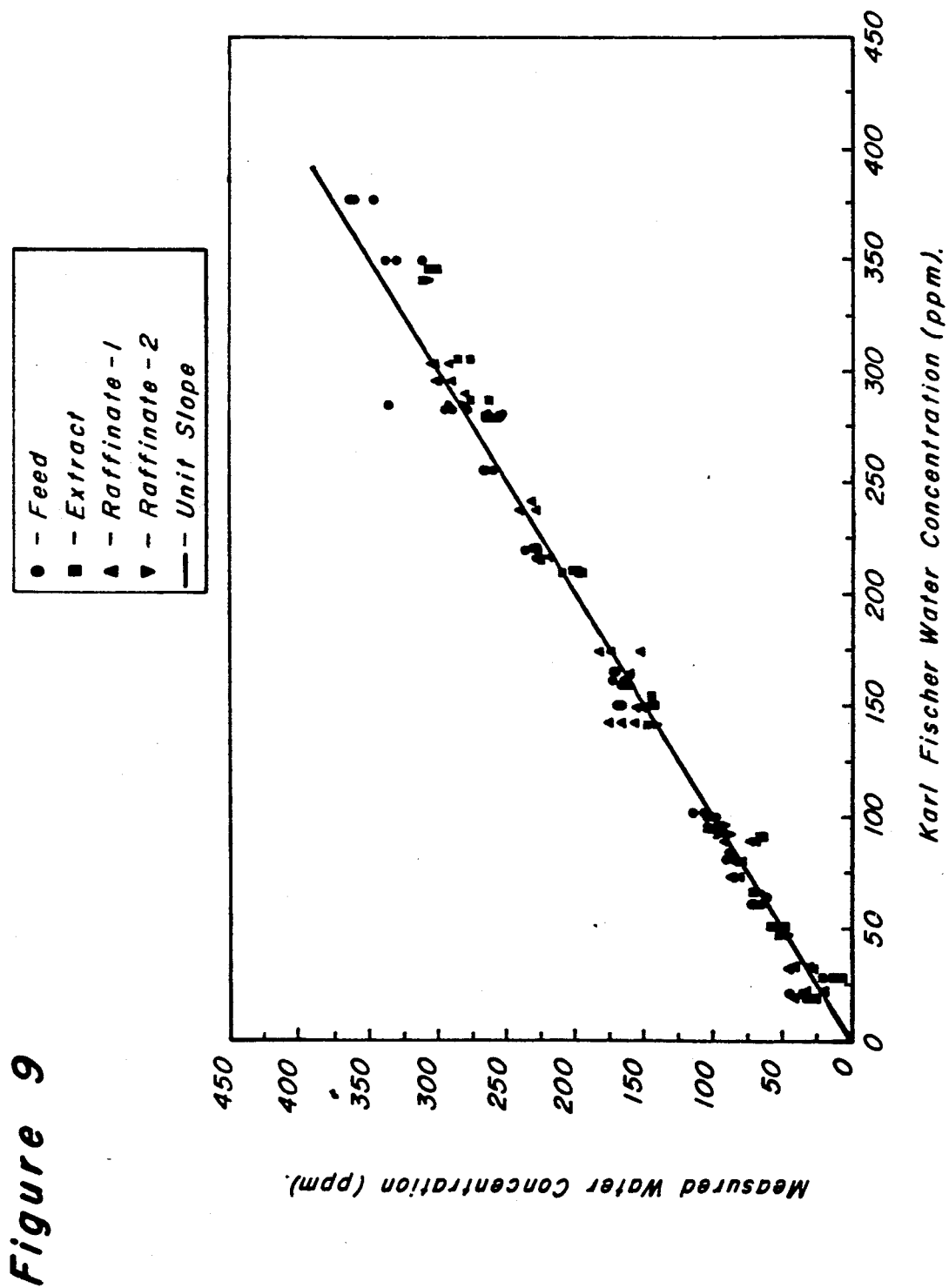

Measurements were made on samples as described in Example 1 using a sample filter having a maximum at 2795 nanometers (55 nm bandwidth) and a reference filter having a maximum at 2580 nanometers (25 nm bandwidth). The scatter in measurement is shown in FIG. 8. However, when an active filter was used (an operational amplifier in combination with a narrow bandpass filter providing an amplified signal at the chopper motor frequency) scatter was significantly reduced, as shown in FIG. 9.

What is claimed is:

1. A method of determining the dissolved water content in a liquid organic phase containing dissolved water at a level of at least about 10 ppm comprising: determining a first and second transmitted light intensity of a first portion of said liquid phase at an infrared frequency within a first interval corresponding to the symmetric OH stretching frequency of water of about 3540 cm$^{-1}$ to about 3640 cm$^{-1}$ and within a second interval of about 3770 cm$^{-1}$ to about 4000 cm$^{-1}$, respectively; forming the ratio of said first and second transmitted light intensity of said first portion to give a first relative light transmittance; determining a first and second transmitted light intensity of a second portion of said liquid organic phase from which water has been removed by drying means to give a dried liquid organic phase containing no more than about 1 ppm water at an infrared frequency within the same first interval corresponding to the symmetric OH stretching frequency of water of about 3540-3640 cm$^{-1}$ and within the same second interval of about 3770-4000 cm$^{-1}$, respectively; forming the ratio of said first and second transmitted light intensity of the dried liquid organic phase to give a second relative light transmittance, and comparing the difference between the logarithms of the first and second relative light transmittance as a measure of the dissolved water content.

2. The method of claim 1 where the second transmitted light intensity is measured over an interval of 150 cm$^{-1}$ within the range of 3770-4000 cm$^{-1}$.

3. The method of claim 2 where the second transmitted light intensity is measured within an interval of not more than about 100 cm$^{-1}$.

4. The method of claim 3 where the second transmitted light intensity is measured within an interval of not more than about 70 cm$^{-1}$.

5. The method of claim 1 where the liquid organic phase is a hydrocarbon.

6. An apparatus for measuring the amount of water dissolved in an organic liquid comprising:
   a radiation source providing a constant intensity beam of infrared radiation having a wavelength range at least from 2.94 to about 2.50 microns;

means for chopping said infrared radiation in the path of infrared radiation and producing a beam of chopped infrared radiation, said means operating at a chopping frequency in the range from about 320 to about 450 cycles per second where the chopping frequency is constant to ±0.1 Hz;

first and second means for filtering the beam of infrared radiation, said first filtering means passing only infrared radiation having a wavelength corresponding to the symmetric OH stretching frequency of water within the range of about 3540 to about 3640 cm$^{-1}$ (2.7100 to about 2.8653 microns) and said second filtering means passing only infrared radiation having a wavelength within the range of about 3770 cm$^{-1}$ to about 4000 cm$^{-1}$ (2.50 to about 2.65 microns), said first and second filtering means positioned in the beam of infrared radiation between the infrared radiation source and an infrared detector;

means for alternately placing said first and second filtering means in the beam of infrared radiation and producing a filtered beam of infrared radiation;

a cell transparent to infrared radiation in said wavelength range comprising means for holding a sample of said organic liquid in the path of the chopped infrared radiation;

an infrared detector having a response to infrared radiation of the wavelengths passed by the first and second infrared radiation filtering means and positioned to detect infrared radiation passing through said sample, said infrared detector being excited by incident infrared radiation of the wavelengths passed by the first and second filtering means and transmitted through the sample cell to produce an electrical signal proportional to the infrared radiation incident upon it; and means to measure the component of the electrical signal generated by the infrared detector at the chopping frequency.

7. The apparatus of claim 6 where said second filtering means has a bandwidth of not more than about 70 cm$^{-1}$.

8. The apparatus of claim 6 where the filtering means are placed in the beam of unchopped infrared radiation.

9. The apparatus of claim 6 where the filtering means are placed in the beam of chopped infrared radiation.

10. A process for sampling a stream of liquid organic phase containing dissolved water in an amount from at least about 10 ppm and determining the dissolved water content comprising: withdrawing a portion of the stream into a sample reservoir; metering an amount of liquid from the sample reservoir into a drying means; drying the liquid in the drying means for a time sufficient to remove water to a level of no more than about 1 ppm to give a dried organic liquid phase; filling a cell transparent to infrared radiation of a wavelength from about 2.50 to about 2.94 microns (4000-3400 cm$^{-1}$) with a portion of the dried organic liquid phase; determining a first and second transmitted light intensity of the dried organic liquid phase at a first infrared frequency corresponding to the symmetric OH stretching frequency of water within an interval of about 3540 cm$^{-1}$ to about 3640 cm$^{-1}$ and at a second infrared frequency within an interval of about 3770 cm$^{-1}$ to about 4000 cm$^{-1}$, respectively, and forming the ratio of said first and second transmitted light intensity to give a first relative transmittance of the dried organic liquid phase; replacing the contents of the infrared cell with a portion of the undried liquid from the sample reservoir; determining a first and second transmitted light intensity of the undried organic liquid phase at the first and at the second infrared frequency, respectively, and forming the ratio of the first and second transmitted light intensities of the undried organic liquid phase to give a second relative transmittance of the undried liquid, and; comparing the difference between the logarithms of the first and second relative transmittances.

11. The process of claim 10 where the drying means is selected from the group consisting of active metal turnings, hydroscopic inorganic oxides, and molecular sieves.

12. The process of claim 11 where the drying means is a molecular sieve.

13. The process of claim 12 where the molecular sieve is selected from the group consisting of zeolites 3A, 4A, and 5A.

14. The process of claim 10 where the second transmitted light intensity is measured over an interval of 150 cm$^{-1}$.

15. The process of claim 14 where the second transmitted light intensity is measured within an interval of not more than about 100 cm$^{-1}$.

16. The process of claim 15 where the transmitted light intensity is measured within an interval of no more than about 70 cm$^{-1}$.

17. The process of claim 10 where the organic phase is a hydrocarbon.

18. A method of determining the dissolved water content in a liquid organic phase containing dissolved water at a level of at least about 10 ppm comprising obtaining a first relative transmittance of a dried portion of the liquid organic phase, obtaining a second relative transmittance of an undried portion of said liquid organic phase, and comparing said first and second relative transmittance as a measure of the dissolved water content where: the relative transmittance is the ratio of light intensity transmitted by the sample at a first frequency corresponding to the symmetric OH stretching frequency of water within an interval of about 3540 cm$^{-1}$ to about 3640 cm$^{-1}$ to the light intensity transmitted by the same sample at a second frequency within an interval of about 3770 cm$^{-1}$ to about 4000 cm$^{-1}$, and; the dried portion of said liquid organic phase is obtained by removing the water from a portion of said liquid organic phase to give a dried liquid organic phase containing no more than about 1 ppm water.

* * * * *